(12) United States Patent
Mischak

(10) Patent No.: US 7,955,862 B2
(45) Date of Patent: Jun. 7, 2011

(54) METHOD AND DEVICE FOR THE QUALITATIVE AND/OR QUANTITATIVE DETERMINATION OF A PROTEIN AND/OR PEPTIDE PATTERN OF A FLUID SAMPLE, WHICH HAS BEEN TAKEN FROM A HUMAN OR ANIMAL BODY

(75) Inventor: Harald Mischak, Sehnde (DE)

(73) Assignee: Mosaiques Diagnostics and Therapeutics AG, Hanover (DE)

( * ) Notice: Subject to any disclaimer, the term of this patent is extended or adjusted under 35 U.S.C. 154(b) by 974 days.

(21) Appl. No.: 10/543,628

(22) PCT Filed: Jan. 27, 2004

(86) PCT No.: PCT/DE2004/000119
§ 371 (c)(1),
(2), (4) Date: Feb. 16, 2006

(87) PCT Pub. No.: WO2004/068130
PCT Pub. Date: Aug. 12, 2004

(65) Prior Publication Data
US 2006/0211076 A1    Sep. 21, 2006

(30) Foreign Application Priority Data

Jan. 31, 2003  (DE) .................... 103 04 106

(51) Int. Cl.
*G01N 27/447* (2006.01)
(52) U.S. Cl. ............ 436/173; 702/19; 702/23; 250/281; 436/86
(58) Field of Classification Search .......... 702/19, 702/23; 436/173
See application file for complete search history.

(56) References Cited

U.S. PATENT DOCUMENTS 7,258,775 B2 *  8/2007  Mischak et al. ............. 204/452
(Continued)

FOREIGN PATENT DOCUMENTS

WO          WO 98/35226          8/1998
(Continued)

OTHER PUBLICATIONS

Mann et al., *Analysis of Proteins and Proteomes by Mass Spectrometry*, Annual Review of Biochemistry 2001, vol. 70, pp. 437-473 (XP-002955539).

John R. Yates, III, *Database searching using mass spectrometry data*, Electrophoresis, Weinheim, DE, vol. 19, 1998, pp. 893-900 (XP002964174).

(Continued)

*Primary Examiner* — Jill Warden
*Assistant Examiner* — Shogo Sasaki
(74) *Attorney, Agent, or Firm* — Thompson Hine LLP

(57) ABSTRACT

Provided are a process and a device for the qualitative and/or quantitative determination of a protein and/or peptide pattern of a liquid sample taken from a human or animal body for checking its state. The peptides and proteins of the liquid sample are processed and then subjected to analysis, wherein reference and sample values describing states of a human or animal body as well as deviations and correspondences derived therefrom are established, automatically stored in a data base, and when the protein and/or peptide pattern is again determined, a search for optimum correspondence is automatically performed. In this process, mass components or structural components of the proteins and/or peptides are established and stored. Subsequently, real masses or real structures are calculated from a common evaluation of the stored mass components or structural components, and an assignment to the proteins and/or peptides contained in the liquid sample is performed from a combination of the calculated real masses or real structures.

4 Claims, 5 Drawing Sheets

U.S. PATENT DOCUMENTS

2003/0132114 A1* 7/2003 Mischak et al. ............. 204/452

FOREIGN PATENT DOCUMENTS

| WO | WO 01/84140 A2 | 11/2001 |
| WO | WO 03/102539 A2 | 12/2003 |

OTHER PUBLICATIONS

English translation of International Preliminary Report on Patentability for PCT/DE/2004/000119, date of mailing Sep. 29, 2005 (10 pages).

* cited by examiner

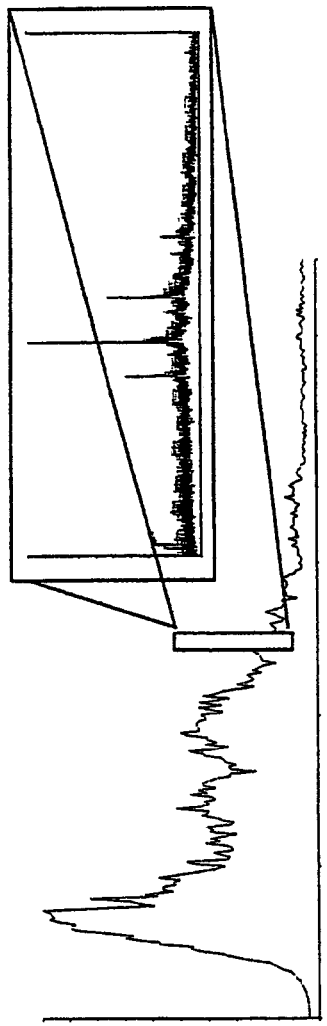
Fig. 2a
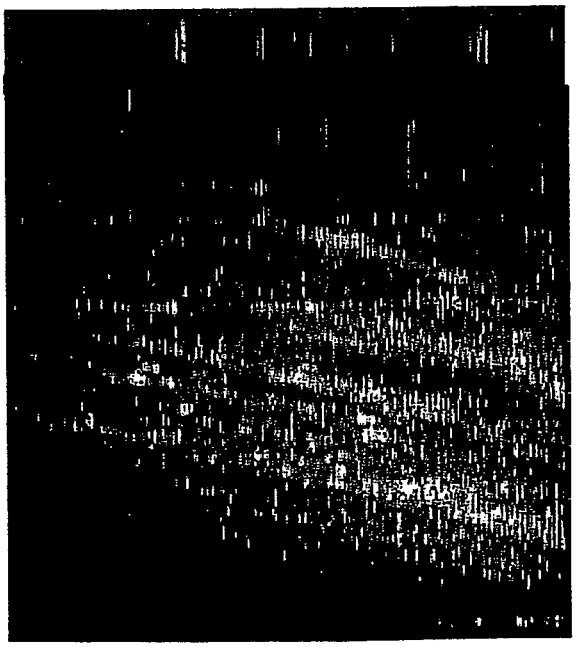
Fig. 2b
| Mass | frequency in normal |
|---|---|
| 1321,13 | 90% |
| 1538,86 | 90% |
| 2256,34 | 90% |
| 1217,71 | 90% |
| 1467,22 | 90% |
| 2989,84 | 90% |
| 4351,15 | 90% |
| 1421,98 | 90% |
| 1424,18 | 90% |
| 1255,23 | 90% |
| 1607,51 | 90% |
| 1157,3 | 90% |
| 1679,21 | 90% |
| 1737,32 | 90% |
| 1910,42 | 90% |
| 2393,32 | 90% |
| 1893,06 | 90% |
| 1933,1 | 90% |
| 2063,36 | 90% |
| 1134,17 | 90% |
| 1178,9 | 90% |
| 1451,12 | 90% |
| 1311,55 | 90% |
Fig. 2c
Fig. 2

| Mass | frequency in normal | normal against MNGN |
|---|---|---|
| 1321,13 | 90% | 25% |
| 1538,86 | 90% | <24% |
| 2256,34 | 90% | <24% |
| 1217,71 | 90% | 25% |
| 1467,22 | 90% | 25% |
| 2999,84 | 80% | <24% |
| 4351,15 | 90% | 90% |
| 1421,98 | 90% | 25% |
| 1424,18 | 90% | 70% |
| 1255,23 | 90% | <24% |
| 1607,51 | 90% | <24% |
| 1157,3 | 90% | 50% |
| 1679,21 | 90% | 90% |
| 1737,32 | 90% | 80% |
| 1910,42 | 90% | <24% |
| 2393,32 | 90% | <24% |
| 1893,06 | 90% | <24% |
| 1933,1 | 90% | 25% |
| 2063,36 | 90% | <24% |
| 1134,17 | 90% | <24% |
| 1178,9 | 90% | <24% |
| 1451,12 | 90% | <24% |
| 1311,55 | 90% | 90% |
| 1194,19 | 90% | <24% |
| 2116,68 | 80% | <24% |
| 1697,51 | 90% | <24% |
| 2408,39 | 90% | <24% |
| 3400,96 | 90% | |
| 1249,62 | 90% | <24% |
| 1948,51 | 90% | 25% |
| 1522,45 | 90% | <24% |
| 1579,93 | 80% | <24% |
| 1434,78 | 80% | 25% |
| 1313,6 | 80% | <24% |
| 2562,42 | 80% | <24% |
| 1238,78 | 90% | |
| 1377,71 | 90% | 50% |
| 1655,17 | 90% | 70% |
| 1679,67 | 90% | 25% |
| 1223,91 | 90% | 25% |
| 1508,02 | 90% | 25% |
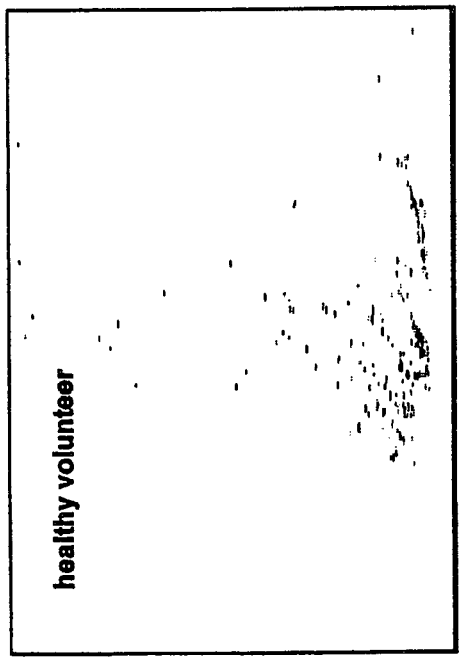
Fig. 3a — healthy volunteer
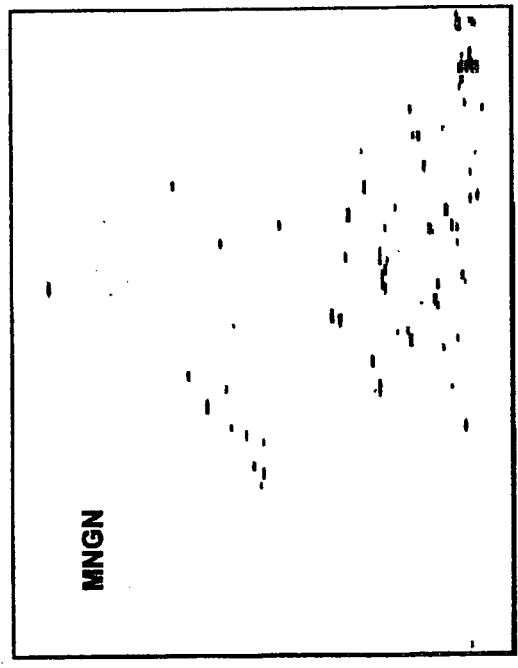
Fig. 3b — MNGN

| Masse | frequency normal | normal against MCG/FSGS |
|---|---|---|
| 1321,13 | 90% | 25% |
| 1538,86 | 90% | <24% |
| 2256,34 | 90% | <24% |
| 1217,71 | 90% | 25% |
| 1467,22 | 90% | 25% |
| 2999,84 | 90% | 25% |
| 4351,15 | 90% | <24% |
| 1421,98 | 90% | 25% |
| 1424,18 | 90% | 70% |
| 1255,23 | 90% | <24% |
| 1607,51 | 90% | <24% |
| 1157,3 | 90% | 50% |
| 1679,21 | 90% | 90% |
| 1737,32 | 90% | 90% |
| 1810,42 | 90% | <24% |
| 2393,32 | 90% | <24% |
| 1893,06 | 90% | <24% |
| 1933,1 | 90% | 25% |
| 2063,36 | 90% | <24% |
| 1134,17 | 90% | <24% |
| 1178,9 | 90% | <24% |
| 1451,12 | 90% | <24% |
| 1311,55 | 90% | 90% |
| 1194,19 | 90% | 50% |
| 2116,68 | 90% | <24% |
| 1697,51 | 90% | <24% |
| 2408,39 | 90% | <24% |
| 3400,96 | 90% | <24% |
| 1249,62 | 90% | 25% |
| 1848,61 | 90% | <24% |
| 1522,45 | 90% | <24% |
| 1579,93 | 90% | <24% |
| 1434,78 | 90% | 25% |
| 1313,6 | 90% | <24% |
| 2562,42 | 90% | 50% |
| 1238,78 | 90% | 70% |
| 1377,71 | 90% | 70% |
| 1655,17 | 90% | 70% |
| 1679,67 | 90% | 25% |
| 1223,91 | 90% | 50% |
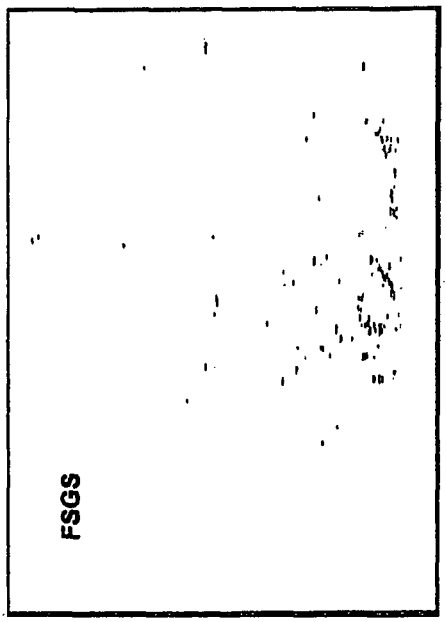
Fig. 3c (FSGS)
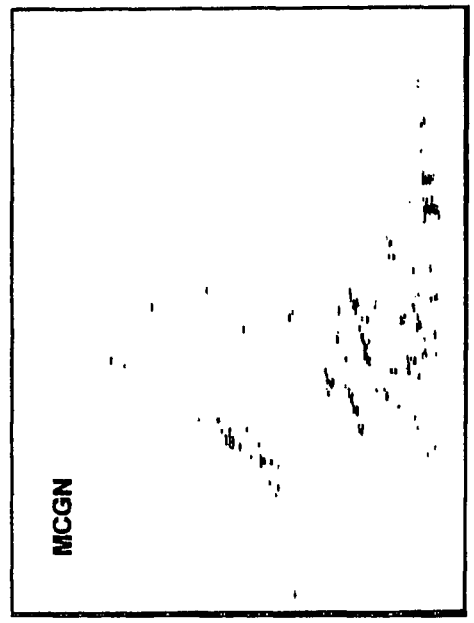
Fig. 3d (MCGN)

METHOD AND DEVICE FOR THE QUALITATIVE AND/OR QUANTITATIVE DETERMINATION OF A PROTEIN AND/OR PEPTIDE PATTERN OF A FLUID SAMPLE, WHICH HAS BEEN TAKEN FROM A HUMAN OR ANIMAL BODY

The invention relates to a process and device for the qualitative and/or quantitative determination of a protein and/or peptide pattern of a liquid sample taken from a human or animal body for checking its state.

From WO 01/84140 A2, a generic process and a generic device for the qualitative and/or quantitative determination of a protein and/or peptide pattern of a liquid sample have been known. Proteins and/or peptides of a liquid sample are separated by means of capillary electrophoresis, then directly ionized and transferred through an interface to an on-line coupled mass spectrometer for detection.

For monitoring the state of a human or animal body over an extended period, reference and sample values describing this state as well as deviations and correspondences derived therefrom are automatically stored in a data base, and when the protein and/or peptide pattern is again determined, a search for optimum correspondence is automatically performed.

It is the object of the invention to establish the proteins and peptides contained in a liquid sample quickly and reproducibly in a common acquisition and evaluation process in a process and a device for the qualitative and/or quantitative determination of a protein and/or peptide pattern of a liquid sample.

In a process and device for the qualitative and/or quantitative determination of a protein and/or peptide pattern of a liquid sample taken from a human or animal body for checking its state this object is achieved by the features stated in the respective claims.

Further developments and advantageous embodiments can be seen from the dependent claims.

Continuous storing of the mass components or structural components of the proteins and/or peptides yields a multidimensional data field of raw data from which real masses or real structures can be independently calculated by means of computational algorithms.

According to one embodiment using determination by mass spectrometry, continuous storing of the individual spectra from the mass spectrometer yields a three-dimensional data field of the overall spectrum, the first dimension representing the amplitude of the spectral lines, the second dimension representing time, and the third dimension representing the mass. Thus, an evaluation by means of computational algorithms can yield precise statements as to the real masses and related overall amplitudes. In this process, all the masses and overall amplitudes are established in a common evaluation process, and a simultaneous assignment to the proteins and/or peptides contained in the liquid sample is available for comparison with stored values.

According to a further development, elimination of the interferences contained in the spectra, especially noise, is performed after the storing of the individual spectra and before the calculation of the real masses and the related overall amplitudes.

Since interferences, especially noise, do not produce any systematically repeating lines in the spectrogram in contrast to wanted signals, interferences can be distinguished from wanted signals, which enables their elimination. The acquisition and resolution of wanted signals is enhanced in this way, so that a higher number of different proteins and/or peptides whose spectral lines have lower amplitudes can be established.

Preferably, only masses and overall amplitudes above preset thresholds are evaluated. This reduces the volume of the data from the evaluated individual spectra and shortens the computing time.

Further, in a new determination of the protein and/or peptide pattern, a calibration of the masses and overall amplitudes can be effected from the masses and overall amplitudes of individual proteins and/or peptides which are stored in the data base as reference values because of their presence in all liquid samples.

In this measure, use is made of the knowledge, obtained from preliminary studies, that some of the proteins and/or peptides which can be determined are constantly present in all liquid samples examined, and also always at approximately the same concentration. This equally holds for samples from donors with normal and deviating results. By using these proteins and/or peptides as references, the raw values of the spectra and thus also the masses and overall amplitudes can be calibrated in a new determination of the protein and/or peptide pattern, and comparisons with stored patterns are facilitated.

In the following, the invention is illustrated by means of an Example and series of experiments performed.

FIG. 2 shows a schematic representation of the course of processing of the measured values to the result;

FIGS. 3a-d show a representation of three-dimensional mass spectra of liquid samples with a normal result and deviating results as well as related Tables.

Figure 4:
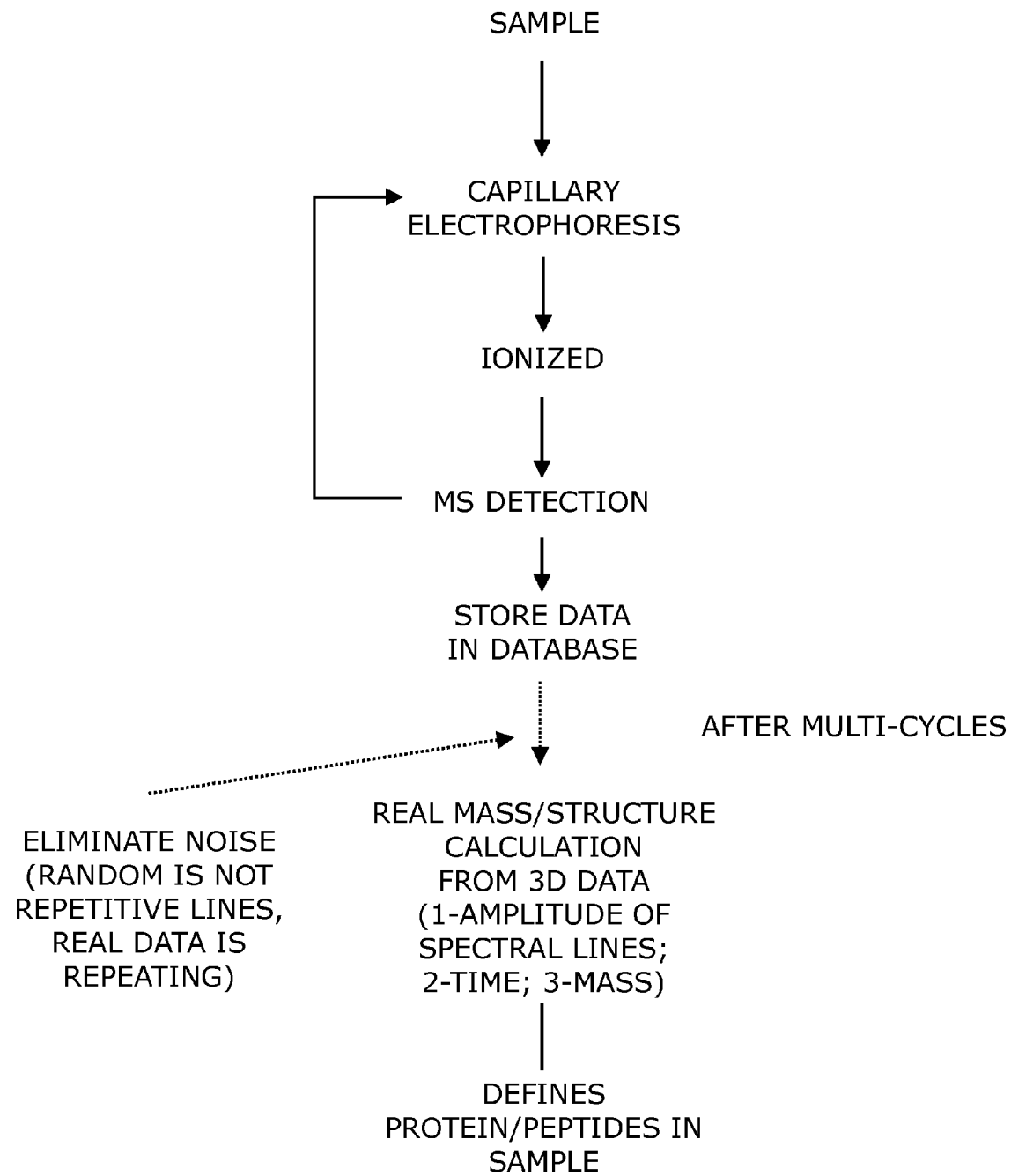

FIG. 4 shows a schematic representation of a process for the determination of a protein and/or peptide pattern of a liquid sample taken from a human or animal body.

Figure 1:
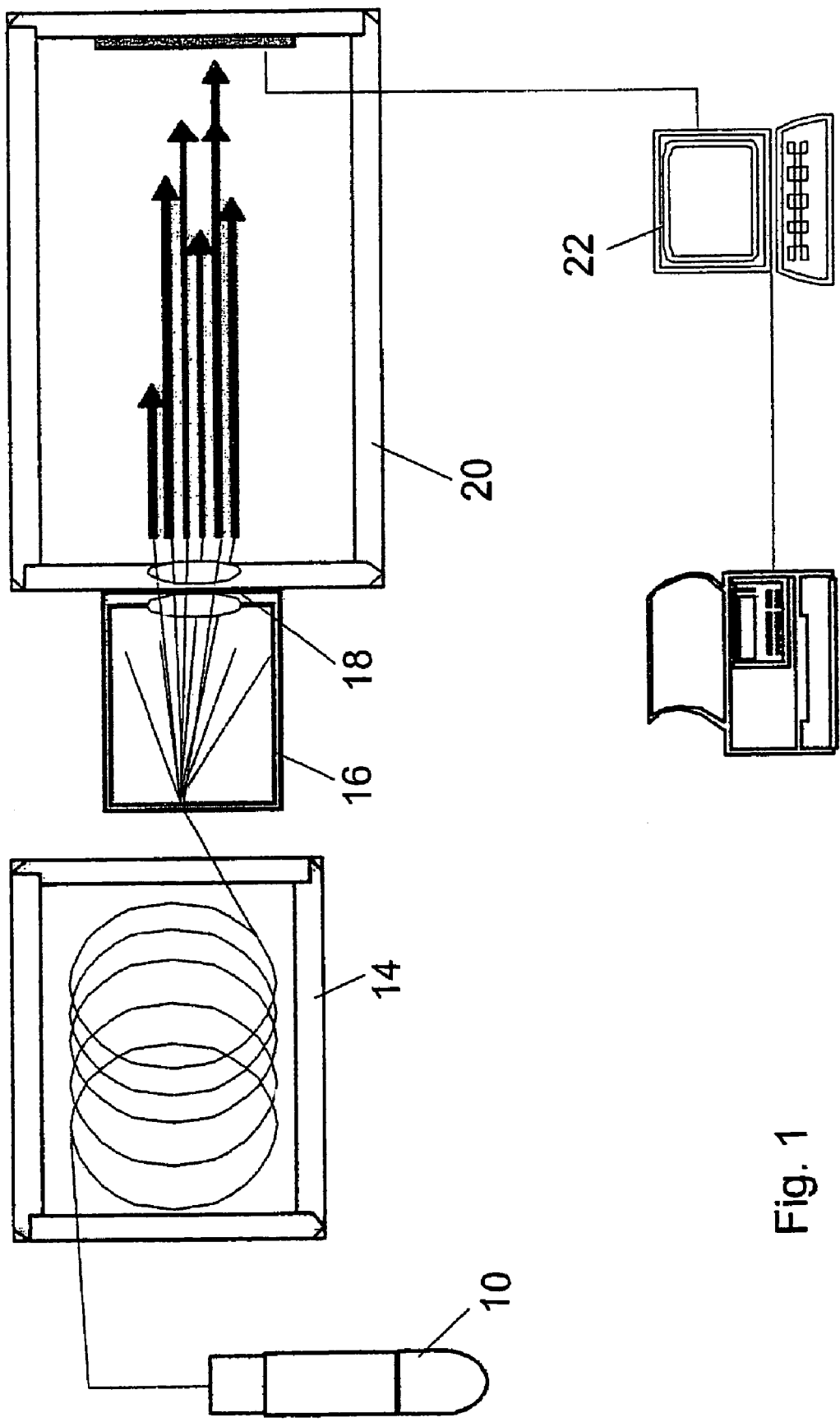
FIG. 1 shows a schematic representation of a device according to the invention.

FIG. 1 shows a schematic representation of a device according to the invention. Fractions obtained by the ultracentrifugation and ultrafiltration of a liquid sample 10, preferably serum or urine, are transferred to a capillary electrophoresis device 14. Through a directly coupled ionization unit 16 and an interface 18, the molecules of the fractions arrive in an on-line coupled mass spectrometer 20. The spectrograms of the mass spectrometer 20 are transferred into a computer unit 22 which comprises a memory and a data base. The program-controlled computer unit 22 serves, on the one hand, for controlling the device. In addition, the measured values obtained by detection are automatically evaluated and stored in data bases. Further, the program automatically compares new measured values with the measured values already stored.

From this comparison, congruent and deviating parameters are established which can be used for describing the state of a human or animal body.

By means of the data bases, it is possible to identify identical, similar or different states of the human or animal body.

The process according to the invention for the qualitative and/or quantitative determination of a protein and/or peptide pattern of a liquid sample taken from a human or animal body can be performed by technically skilled persons. The application does not require a physician and need not be effected in medical laboratories.

FIG. 2 shows a schematic representation of the course of processing of the measured values to the result. In FIG. 2A, the rough course of intensities is represented over the whole measuring period. For a time slot of about 3 seconds from the course of intensities, the related spectrogram is shown. The FIG. 2B image shows a three-dimensional representation of all spectrograms during a measuring period. The time axis which is the first dimension runs from right to left. The intensity axis is represented by brightness. The mass axis runs from top to bottom to top. After elimination of interferences, and using computational algorithms, the computer unit establishes the real mass and the overall amplitudes from all individual spectra. In a first data analysis, all the peaks are identified. In the next step, the charge of each peak is determined, using both the isotope distribution and conjugated masses. Finally, a table of the real masses which occur with a probability of more than 90% in all liquid samples examined is shown in FIG. 2C.

FIGS. 3a-d show a representation of typical examples of three-dimensional mass spectra of liquid samples with a normal result and deviating results, namely MNGN (membranous glomerulonephritis), MCG (minimal change glomerulonephritis) and FSGS (focal segmental glomerulosclerosis), and related tables. Each pathological result shows a typical protein pattern. Subdivided according to the different diseases, the data of the examinations were evaluated statistically and compared with the data from healthy subjects. A number of polypeptides which are present in the healthy subjects could not be detected in subjects with pathological results, while additional polypeptides could be found only in subjects with pathological results, but not in the healthy subjects. Thus, protein patterns which are typical of particular diseases can be established.

The following procedure was used to achieve the results. All subjects were examined beforehand by means of renal biopsies. A group of 18 normal subjects of comparable sex and age having a normal kidney function were examined in order to establish a normal peptide pattern in the urine. Urine samples from all subjects were collected in the morning. The samples were stored at −70° C. For sample processing, the samples were thawed, and 2 ml thereof was fractionated over a Pharmacia C2 column to enrich polypeptides and remove salt, urea and other interfering components. Polypeptides were eluted with 50% acetonitrile in water with 0.5% formic acid. The eluate was lyophilized and taken up in 20 µl of water.

The mobile phase contained 30% methanol and 0.5% formic acid in water. The same liquid was employed as a carrier liquid, the samples were injected under pressure (1 psi for 10 seconds) with 300 nl/min, which corresponds to about 100 nl of sample. The measuring run was performed at 30 kV and 0.2 psi for 45 min.

As shown in Table 1, 51 polypeptides could be found in more than 90% of the normal urine samples. In addition, 70 polypeptides could be found in >70% of the samples, and additional 183 polypeptides could be found in >50% of all samples. The use of this method allowed about 1000 polypeptides to be detected in one sample. About 300 of these polypeptides could be found in more than 50% of the healthy subjects. The data allowed a normal pattern to be established. Thirteen urine samples from subjects with minimal change glomerulonephritis (MCGN), 13 with membranous GN (MNGN) and 7 with focal segmental glomerulosclerosis (FSGS) were compared with the normal patterns.

Three polypeptides which were found in more than 90% of all samples were used as an internal standard. Seventeen polypeptides were found exclusively in more than 90% of the MCGN subjects. Seventeen other polypeptides were found exclusively in MNGN subjects. Three polypeptides of 1312, 1679 and 1737 Da were present in all samples. These were employed as internal standards to ensure comparability. The reproducibility of these data allowed a differential diagnosis of the glomerulonephritides on the basis of the polypeptide spectra. Thus, a comparison of the polypeptide spectra derived from urine samples enabled the three different forms of glomerulonephritis to be distinguished.

In the next step, 33 subjects with nephritis were examined. The data are summarized in Table 2. All the subjects previously obtained different regimens of immunosuppressives for therapy, and 19 thereof obtained low doses of corticosteroid and/or cyclosporin A at the time of the examination. Nephrotic proteinuria could be detected in 2 subjects, with a protein excretion of >3.5 g per day. Twelve subjects showed from 3.5 to 0.5 g of protein per day in the urine, 3 subjects showed from 0.5 to 0.15 g/day, and 16 subjects were in clinical remission with <0.15/day proteinuria and normal serum creatinin.

The data from the individual examinations were grouped in data bases (one for each of the three diseases). The values from these data bases which represent the typical protein patterns were subsequently compared. Significant homologies were found in each disease group. A comparison of the polypeptide patterns could be employed for a retrospective differential diagnosis. Typical examples of spectra from subjects with MNGN, MCG and FSGS are shown in FIG. 3. Each disease shows a typical protein pattern. Subdivided according to the different diseases, the data from the examinations were evaluated statistically and compared with the data from the healthy subjects. A number of polypeptides which are present in the healthy subjects could not be detected in the diseased subjects, while additional polypeptides could be found only in the diseased subjects, but not in the healthy subjects. Thus, protein patterns which are typical of particular diseases can be established.

Table 3 shows the summary of 122 polypeptides which were found in more than 70% of the normal controls, in comparison with the three disease groups. A number of proteins were lacking in the diseased subjects. Although the majority of the MCG subjects were in clinical remission, 56 polypeptides which are present in the normal control could be found in only <25% of the samples from diseased subjects. Nine polypeptides which were found in >90% of the normal controls were lacking in subjects with MNGN. Forty-seven other polypeptides could be detected in <25% of this subject group. In this group too, a number of polypeptides could be found which were lacking in the normal control or in other diseases. Seventeen polypeptides could be identified which were specifically present in MNGN, but in <25% of the MCG or FSGS subjects. One polypeptide could never be detected in healthy subjects. Seventeen other polypeptides could be detected only in the urine from subjects with MCG. This is all the more remarkable since most of these subjects were in clinical remission.

The abbreviations employed have the following meanings:
MNGN membranous glomerulonephritis
FSGS focal segmental glomerulosclerosis
MCGN or MCG minimal change glomerulonephritis

TABLE 1

| Sex | Age | Diagnosis | S-creatinine µM/l | protein g/d | Therapy |
| --- | --- | --- | --- | --- | --- |
| m | 18 | FSGS | 99 | 0.05 | CSA |
| f | 26 | FSGS | 150 | 11.0 | CSA + CS |
| m | 63 | FSGS | <93 | 0.05 | CS |
| f | 49 | FSGS | 80 | 0.05 | CSA + CS |
| m | 63 | FSGS | 95 | 0.02 | CS |
| f | 39 | FSGS | 75 | 2.0 | CSA + CS |
| f | 41 | FSGS | 16 | 0.7 | CSA |
| m | 38 | MNGN | 100 | 0.4 | CSA + CS |

TABLE 1-continued

| Sex | Age | Diagnosis | S-creatinine μM/l | protein g/d | Therapy |
|---|---|---|---|---|---|
| m | 43 | MNGN | 82 | 0.7 | CS |
| f | 32 | MNGN | 83 | 5.0 | CSA + CS |
| m | 36 | MNGN | 93 | 0.2 | CS |
| m | 48 | MNGN | 100 | 1.0 | CSA + CS |
| f | 68 | MNGN | 150 | 1.0 | — |
| m | 47 | MNGN | 93 | 3.0 | CS |
| m | 69 | MNGN | 128 | 0.02 | CSA |
| f | 34 | MNGN | <80 | 3.0 | CSA + CS |
| f | 21 | MNGN | 80 | 1.0 | CSA + CS |
| m | 23 | MNGN | 150 | 0.3 | — |
| m | 44 | MNGN | 118 | 1.0 | CSA |
| m | 40 | MNGN | 119 | 1.0 | CSA |
| m | 21 | MCGN | 57 | 0.12 | — |
| f | 43 | MCGN | 114 | 0.01 | CSA |
| m | 45 | MCGN+ | <93 | 0.01 | — |
| m | 61 | MCGN+ | <93 | 0.1 | — |
| f | 52 | MCGN+ | 118 | 0.01 | — |
| f | 44 | MCGN+ | <80 | 0.02 | CSA |
| m | 39 | MCGN* | <93 | 0.02 | — |
| f | 70 | MCGN* | 95 | 0.08 | — |
| m | 68 | MCGN | <93 | 0.08 | — |
| m | 50 | MCGN | <93 | 0.05 | — |
| m | 18 | MCGN | 77 | 0.05 | CSA + CS |
| f | 28 | MCGN | 160 | 0.1 | — |
| m | 52 | MCGN | 93 | 0.4 | CS |

+frequent relapse;
Therapy: immunosuppression;
CSA Ciclosporin A,
*DD FSGS
CS: corticosteroids;
—: currently no immunosuppression

TABLE 2

| Mass | frequency normal [%] | normal vs MCG/FSGS [%] | normal vs MNGN [%] |
|---|---|---|---|
| 1134.17 | >90 | <25 | <25 |
| 1157.30 | >90 | >50 | >50 |
| 1178.90 | >90 | <25 | <25 |
| 1194.19 | >90 | >50 | <25 |
| 1217.71 | >90 | 25-50 | 25-50 |
| 1223.91 | >90 | >50 | 25-50 |
| 1238.78 | >90 | >70 | |
| 1249.62 | >90 | <25 | <25 |
| 1255.23 | >90 | <25 | <25 |
| 1311.55 | >90 | >90 | >90 |
| 1313.43 | >90 | <25 | >50 |
| 1313.60 | >90 | <25 | <25 |
| 1315.54 | >90 | 25-50 | 25-50 |
| 1321.13 | >90 | 25-50 | 25-50 |
| 1377.71 | >90 | >70 | >50 |
| 1421.98 | >90 | 25-50 | 25-50 |
| 1424.18 | >90 | >70 | >70 |
| 1434.78 | >90 | 25-50 | 25-50 |
| 1451.12 | >90 | <25 | <25 |
| 1467.22 | >90 | 25-50 | 25-50 |
| 1508.02 | >90 | 25-50 | 25-50 |
| 1522.45 | >90 | <25 | <25 |
| 1538.86 | >90 | <25 | <25 |
| 1539.09 | >90 | <25 | <25 |
| 1579.93 | >90 | <25 | <25 |
| 1607.51 | >90 | <25 | <25 |
| 1635.13 | >90 | <25 | <25 |
| 1655.17 | >90 | >70 | >70 |
| 1679.21 | >90 | >90 | >90 |
| 1679.67 | >90 | 25-50 | 25-50 |
| 1697.51 | >90 | <25 | <25 |
| 1715.38 | >90 | <25 | <25 |
| 1737.32 | >90 | >90 | >90 |
| 1893.06 | >90 | <25 | <25 |
| 1894.62 | >90 | <25 | <25 |
| 1910.42 | >90 | <25 | <25 |
| 1933.10 | >90 | 25-50 | 25-50 |
| 1948.51 | >90 | 25-50 | 25-50 |
| 2047.25 | >90 | <25 | >50 |
| 2063.36 | >90 | <25 | <25 |
| 2116.68 | >90 | <25 | <25 |
| 2256.34 | >90 | <25 | <25 |
| 2393.32 | >90 | <25 | <25 |
| 2408.39 | >90 | <25 | <25 |
| 2562.42 | >90 | >50 | <25 |
| 2999.84 | >90 | 25-50 | <25 |
| 3279.82 | >90 | >50 | |
| 3400.96 | >90 | <25 | |
| 4351.15 | >90 | <25 | >90 |
| 4679.60 | >90 | <25 | >50 |
| 1027.85 | >70 | <25 | |
| 1071.62 | >70 | 25-50 | 25-50 |
| 1081.30 | >70 | <25 | <25 |
| 1141.29 | >70 | 25-50 | 25-50 |
| 1160.14 | >70 | <25 | <25 |
| 1191.11 | >70 | 25-50 | 25-50 |
| 1195.07 | >70 | >50 | <25 |
| 1199.44 | >70 | >90 | >90 |
| 1200.07 | >70 | <25 | <25 |
| 1235.05 | >70 | 25-50 | 25-50 |
| 1261.15 | >70 | 25-50 | 25-50 |
| 1265.14 | >70 | <25 | <25 |
| 1275.68 | >70 | <25 | <25 |
| 1282.87 | >70 | 25-50 | 25-50 |
| 1297.21 | >70 | 25-50 | >50 |
| 1307.92 | >70 | 25-50 | 25-50 |
| 1311.78 | >70 | >90 | >90 |
| 1367.23 | >70 | <25 | <25 |
| 1368.21 | >70 | <25 | <25 |
| 1389.44 | >70 | 25-50 | 25-50 |
| 1421.44 | >70 | 25-50 | 25-50 |
| 1424.54 | >70 | >70 | >70 |
| 1438.12 | >70 | >50 | 25-50 |
| 1445.96 | >70 | <25 | <25 |
| 1461.66 | >70 | 25-50 | 25-50 |
| 1472.92 | >70 | 25-50 | 25-50 |
| 1545.48 | >70 | <25 | <25 |
| 1561.03 | >70 | 25-50 | 25-50 |
| 1578.80 | >70 | 25-50 | 25-50 |
| 1589.00 | >70 | >50 | <25 |
| 1635.96 | >70 | <25 | <25 |
| 1651.06 | >70 | 25-50 | 25-50 |
| 1753.81 | >70 | 25-50 | 25-50 |
| 1761.26 | >70 | >50 | >50 |
| 1765.48 | >70 | 25-50 | 25-50 |
| 1766.87 | >70 | 25-50 | 25-50 |
| 1875.54 | >70 | 25-50 | 25-50 |
| 1877.49 | >70 | 25-50 | 25-50 |
| 1888.56 | >70 | 25-50 | 25-50 |
| 1913.25 | >70 | >50 | 25-50 |

| Mass | frequency normal | normal against MCG/FSGS | normal against MNGN |
|---|---|---|---|
| 1931.91 | >70 | 25-50 | 25-50 |
| 1947.41 | >70 | >90 | >90 |
| 2007.20 | >70 | 25-50 | 25-50 |
| 2045.33 | >70 | >50 | >50 |
| 2068.65 | >70 | <25 | <25 |
| 2174.04 | >70 | <25 | >70 |
| 2248.28 | >70 | 25-50 | 25-50 |
| 2312.87 | >70 | <25 | <25 |
| 2546.77 | >70 | <25 | <25 |
| 2568.70 | >70 | <25 | <25 |
| 2662.29 | >70 | 25-50 | 25-50 |
| 2678.14 | >70 | <25 | <25 |
| 2694.10 | >70 | 25-50 | 25-50 |
| 2735.76 | >70 | <25 | <25 |
| 2741.39 | >70 | <25 | <25 |
| 2824.26 | >70 | <25 | 25-50 |
| 2888.20 | >70 | | |
| 3010.32 | >70 | >50 | 25-50 |
| 3264.36 | >70 | <25 | <25 |
| 3384.47 | >70 | <25 | |
| 3439.94 | >70 | 25-50 | <25 |

TABLE 2-continued

| | | | |
|---|---|---|---|
| 3456.69 | >70 | <25 | <25 |
| 3478.40 | >70 | >50 | <25 |
| 3721.63 | >70 | 25-50 | 25-50 |
| 3968.61 | >70 | <25 | 25-50 |
| 4041.83 | >70 | 25-50 | |
| 4096.96 | >70 | <25 | <25 |
| 4746.25 | >70 | 25-50 | 25-50 |
| 5799.20 | >70 | <25 | <25 |
| 6169.19 | >70 | <25 | <25 |
| 6183.91 | >70 | <25 | <25 |

TABLE 3

Markers for MNGN and MCG

| mass | MCGN [%] | Normal [%] | MNGN [%] |
|---|---|---|---|
| 1193.95 | >90 | 25-50 | 25-50 |
| 1259.13 | >90 | <25 | <25 |
| 1265 | >90 | <25 | 25-50 |
| 1435.07 | >90 | <25 | <25 |
| 1523.16 | >90 | 25-50 | 25-50 |
| 1538.77 | >90 | <25 | <25 |
| 1561.05 | >90 | <25 | <25 |
| 1635.99 | >90 | <25 | <25 |
| 1651.03 | >90 | 25-50 | 25-50 |
| 1679.08 | >90 | <25 | <25 |
| 1680.33 | >90 | <25 | <25 |
| 1910.6 | >90 | <25 | <25 |
| 2409.04 | >90 | <25 | <25 |
| 2824.47 | >90 | <25 | <25 |
| 3208.58 | >90 | 25 | 25 |
| 3441.19 | >90 | <25 | <25 |
| 3456.4 | >90 | 25-50 | 25-50 |
| 1108.21 | >90 | 25-50 | 25-50 |
| 1386.38 | >90 | 0 | 25-50 |
| 1737.36 | >90 | 0 | 25-50 |
| 1781.24 | >90 | <25 | <25 |
| 1797.24 | >90 | <25 | <25 |
| 1850.6 | >90 | 0 | <25 |
| 2227.55 | >90 | <25 | <25 |
| 2405.97 | >90 | 0 | 0 |
| 2751.55 | >90 | 0 | <25 |
| 3841.38 | >90 | <25 | <25 |
| 4152.6 | >90 | <25 | <25 |
| 4239.56 | >90 | 0 | <25 |
| 4624.34 | >90 | <25 | <25 |
| 4711.49 | >90 | <25 | <25 |
| 4891.54 | >90 | <25 | <25 |
| 5755.82 | >90 | 0 | <25 |
| 5869.67 | >90 | 0 | <25 |

The invention claimed is:

1. A process for the determination of a protein and/or peptide pattern of a liquid sample taken from a human or animal body, the process comprising the steps of:
    separating the liquid sample into fractions, providing separation time for each fraction,
    analyzing the fractions with a mass spectrometer providing masses and amplitudes,
    generating three-dimensional spectrum of the liquid sample, the first dimension representing the amplitude of the spectral lines, the second dimension representing separation time, and the third dimension representing the mass, and
    evaluating the three-dimensional spectrum to yield real separation time, real masses and related overall amplitudes of the proteins and/or peptides of the liquid sample, wherein the real time, real masses, and related overall amplitudes are a protein and/or peptide pattern of the sample.

2. The process of claim 1 wherein the three-dimensional spectrum is obtained by separating the liquid samples by capillary electrophoresis followed by direct ionization and a transfer through an interface to an on-line coupled mass spectrometer for detection.

3. The process according to claim 1 or claim 2, wherein interferences contained in the three-dimensional spectrum are eliminated after storing of the three-dimensional spectra and before the evaluation of the three-dimensional spectra.

4. The process of claim 1 wherein only masses and overall amplitudes above preset thresholds are evaluated.

* * * * *

UNITED STATES PATENT AND TRADEMARK OFFICE
CERTIFICATE OF CORRECTION

| | | |
|---|---|---|
| PATENT NO. | : 7,955,862 B2 | Page 1 of 1 |
| APPLICATION NO. | : 10/543628 | |
| DATED | : June 7, 2011 | |
| INVENTOR(S) | : Mischak | |

It is certified that error appears in the above-identified patent and that said Letters Patent is hereby corrected as shown below:

Claim 2, Column 8, Line 32: "samples" should read -- sample --

Signed and Sealed this
Sixth Day of September, 2011

David J. Kappos
*Director of the United States Patent and Trademark Office*